United States Patent [19]

Taglialatela et al.

[11] Patent Number: 5,270,472
[45] Date of Patent: Dec. 14, 1993

[54] ALKANOYL L-CARNITINE AMIDES WITH AMINOACIDS AND PHARMACEUTICAL COMPOSITIONS CONTAINING SAME FOR PROMOTING REGENERATION OF THE NERVOUS TISSUE, INHIBITING NEURONAL DEGENERATION, ENHANCING THE PROCESS OF LEARNING AND MEMORY AND FOR THE TREATMENT OF COMA

[75] Inventors: Giulio Taglialatela; Nicola Fanto, both of Rome; Mosé Santaniello, Casoria; Claudio Cavazza, Rome, all of Italy

[73] Assignee: Sigma-Tau Industrie Farmaceutiche Riunite S.p.A., Rome, Italy

[21] Appl. No.: 883,388

[22] Filed: May 15, 1992

[30] Foreign Application Priority Data

May 16, 1991 [IT] Italy ........................ RM91 A000333

[51] Int. Cl.$^5$ ............................................ C07C 67/02
[52] U.S. Cl. .................................................... 560/251
[58] Field of Search ........................................ 560/251

*Primary Examiner*—José G. Dees
*Assistant Examiner*—Joseph M. Conrad
*Attorney, Agent, or Firm*—Oblon, Spivak, McClelland, Maier & Neustadt

[57] ABSTRACT

Amides of alkanoyl L-carnitines of general formula (1).

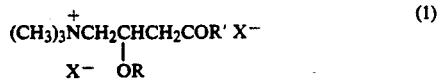

wherein

R is a straight or branched alkanoyl group having from 2 to 8 carbon atoms selected from acetyl, propionyl, butyryl, isobutyryl, valeryl, isovaleryl, hexanoyl, 1-methylbutyryl, t-butylacetyl, 2-ethylbutyryl, 3-methylvaleryl, 4-methylvaleryl, 2-ethylhexanoyl and 2-propylpentanoyl;

R' is the monovalent residue of a naturally occurring aminoacid selected from:

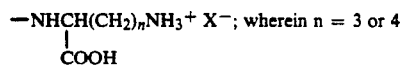

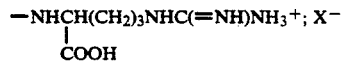

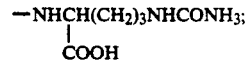

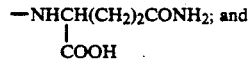

$X^-$ is the anion of a pharmacologically acceptable acid are active in regenerating the nervous tissue, inhibiting neuronal degeneration, enhancing the processes of learning and memory and for the treatment of coma.

Orally or parenterally administrable compositions in unit dosage form comprise between about 50 and about 500 mg of an amide of formula (1).

14 Claims, No Drawings

ALKANOYL L-CARNITINE AMIDES WITH AMINOACIDS AND PHARMACEUTICAL COMPOSITIONS CONTAINING SAME FOR PROMOTING REGENERATION OF THE NERVOUS TISSUE, INHIBITING NEURONAL DEGENERATION, ENHANCING THE PROCESS OF LEARNING AND MEMORY AND FOR THE TREATMENT OF COMA

The present invention relates to amides of alkanoyl L-carnitine of general formula (1)

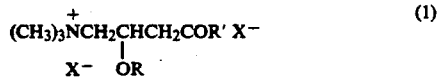

wherein

R is a straight or branched alkanoyl group having from 2 to 8 carbon atoms selected from acetyl, propionyl, butyryl, isobutyryl, valeryl, isovaleryl, hexanoyl, 1-methylbutyryl, t-butylacetyl, 2-ethylbutyryl, 3-methylvaleryl, 4-methylvaleryl, 2-ethylhexanoyl and 2-propylpentanoyl;

R' is the monovalent residue of a naturally occurring aminoacid selected from:

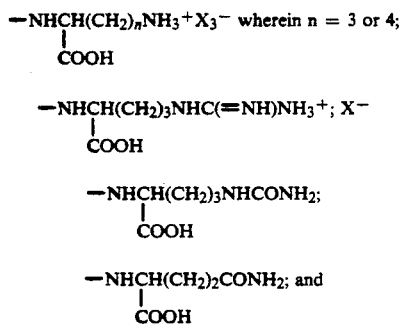

$X^-$ is the anion of a pharmacologically acceptable acid.

The aminoacids corresponding to the above-mentioned residues are ornithine, lysine, arginine, citrulline and glutamine, respectively.

When R' is the residue of glutamine or citrulline, the counterion associated with the aminoacid moiety is obviously missing.

It should be furthermore clearly understood (as it will be on the other hand wholly apparent to the average-skilled expert in organic synthesis) that, although the compounds of the present invention are represented for the sake of simplicity only by formula (1) wherein both the carnitine moiety and the aminoacidic moiety are shown to be associated with the counterion $X^-$ and the carboxyl group on the aminoacidic moiety is shown in protonated form, there are also encompassed within the scope of the present invention the compounds that, depending on reaction conditions, pII etc., can occur as partly salified or inner salts.

In other words, object of the present invention are also the compounds of formula (1) wherein one or both $X^-$ can be missing and the aminoacidic carboxyl can occur either as protonated or unprotonated group. Moreover, when two $X^-$ occur in a compound of this invention, they could be derived from different pharmacologically acceptable acids.

The compounds of formula (1) are active in promoting regeneration of the nervous tissue, inhibiting neuronal degeneration (as it occurs e.g. in Alzheimer's senile dementia and Parkinson's disease) and in the treatment of coma.

These compounds are, furthermore, potent enhancers of learning and memory processes.

The present invention also relates to orally or parenterally administrable pharmaccutical for the treatment of the foregoing diseases and for enhancing the learning and memory processes, which comprise a compound of formula (1) as active ingredient and a pharmacologically acceptable excipient.

The anion of the pharmacologically acceptable acid is for instance selected from: chloride, bromide, iodide, orotate, acid aspartate, acid citrate, acid phosphate, acid fumarate, lactate, acid maleate, acid oxalate, acid sulphate and glucosephate.

Among the compounds of formula (1), the following are particularly preferred:

acctyl L-carnitinamide of L-arginine;
propionyl L-carnitinamide of L-arginine;
acetyl L-carnitinamide of L-ornithine;
acetyl L-carnitinamide of citrulline;
acetyl L-carnitinamide of L-glutamine; and
isovaleryl L-carntinamide of L-arginine.

Amides aof alkanoylcarnitines were already known (see U.S. Pat. No. 4,443,475). These amides (e.g. propionylcarnitine amide of taurne), in addition to their structure other than that of compounds (1), are effective in the treatment of functional arrhythmias and arrhythmias secondary to myocardial sclerotic diseases and as psychostimulants and, therefore, exhibit therapeutic properties entirely different and unrelated from those of the compounds of the present invention.

Also carnitine derivatives with aminoacids are already known, for instance from U.S. Pat. No. 4,812,478. These compounds are, however, esters (on carnitine hydroxyl), not amides; furthermore, these esters are effective as liver protecting agents and, therefore, structurally and pharmacologically remote from the compounds of the present invention.

The compounds of formula (1) are prepared (e.g. as chlorides hydrochlorides) via the following reaction scheme:

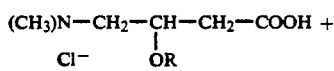

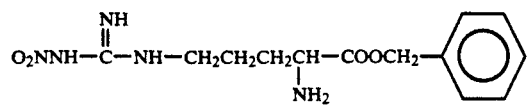

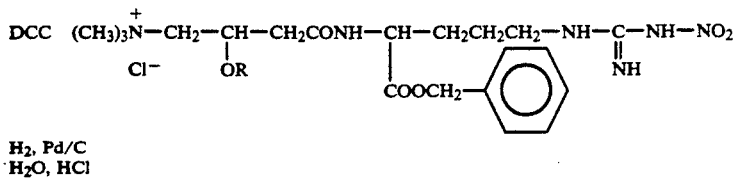

H₂, Pd/C
H₂O, HCl compounds of formula (1).

The following non limiting examples describe the preparation of some compounds of the invention.

EXAMPLE 1

Preparation of L-acetyl L-carnitinamide of L-arginine chloride hydrochloride (ST 857).

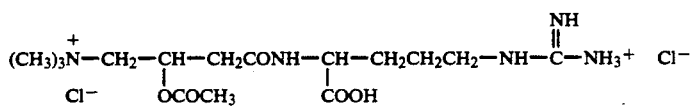

(M.W. 432,35)

A solution of 24 g (0.1 moles) acetyl L-carnitine chloride (M.W. 239.70) in 35 mL water was added to a solution of 30.9 g (0.1 moles) N^ω-nitro-L-arginine benzyl ester (M.W. 309.33) (Collection Czechslov. Chem. Cominun. 41. 3467; 1978) in 150 mL tetrahydrofuran.

To the resulting solution cooled to 0° C., a solution of 20.6 g (0.1 moles) dicyclohexylcarbodiimide (M.W. 206,33) in 50 mL tetrahydrofuran was added over a period of 2 hours, keeping the temperature between 0° C. and +5° C.

The resulting mixture was kept under stirring for 48 hours at room temperature, the precipitate was filtered off and the filtrate concentrated to dryness under reduced pressure.

The residue was taken up with 50 mL methanol and the solution thus obtained added dropwise to 1 L ethyl ether.

The liquid was decanted and the treatment with methanol-ethyl ether was repeated on the solid residue. By filtration, a pitchy solid was obtained which was oven-dried at 30° C. under a residual vacuum of 1 mm Hg.

45 g (yield 85%) acetyl L-carnitinamide of N^ω-nitro-L-arginine benzyl ester chloride were obtained which were dissolved in 200 mL water. To the resulting solution, 7 mL concentrated hydrochloric acid and 7 g 10% Pd/C were added and the resulting mixture was hydrogenated at 3 atmospheres and 20° C.

When the theoretically calculated amount of hydrogen was used up, the suspension was filtered on celite and the filtrate lyophilized.

34 g (yield 92.8%) acetyl L-carnitinamide of L-arginine chloride hydrochloride were obtained as a highly hygroscopic, vitreous, white solid.

TLC: single spot
Eluant:CHCl₃:MeOH:H₂O:IsoPrOH:AcOH 60:40:15:10:15:)

Silica gel plates 0.25 mm = 60 F₂₅₄ (E. Merck)
Detectors: UV 254 nm and iodine vapours Elemental analysis (C₁₅H₃₁Cl₂N₂O₅): Calc %: C 41.67; H 7.23; Cl 16.40; N 16.20; Found %: C 41.38; H 7.54; Cl 16.27; N 16.15.

HPLC: Waters 510 column μBondapack-NH₂(10μ), inner diameter=3.9 mm length 300 mm
mobile phase CH₃CN/KH₂PO₄ 0.05M in H₂O 65:35
Flow rate: 1 mL/min Detector UV: HP 1040A λ=205 nm
Capacity factor (K')=5.29
¹H-NMR: VARIAN 300 MHz(D₂O)δ=1.-58-1.92(4H, m, CH₂CH₂); 2.14(3H,s,CH₃CO); 2.74(2H,d,CH₂CON<); 3.19(9H,s, (CH₃)₃N); 3.22(2H,m,CH₂NH); 3.64-3.95(2H,m,CH₂N-(CH₃)₃); 4.20(1H,m,CHNH); 5.70(1H,m,CHOCOCH₃)
¹³C-NMR:
Varian 300 MHz(D₂O) (p.p.m): 180.08; 175.43; 173.20; 159.67; 70.71; 68.69; 57.00; 56.84; 43.53; 41.45; 31.22; 27.48; 23.43.
F.T.I.R.
Nicolet 20 S x C, V_max Kbr (cm⁻¹): broad band between 3600 and 2400; 1742; 1661; 1547; 1230
[α]_D^25 = −17.9° (c=1 in H₂O)

EXAMPLE 2

Preparation of propionyl L-carnitinamide of L-arginine chloride hydrochloride (ST 921).

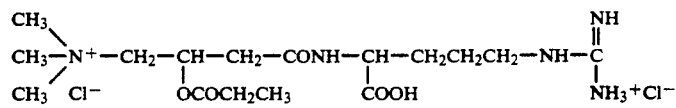

To 20 g (0.065 moles) L-nitroarginine benzyl ester in 110 mL tetrahydrofuran, 16.44 g (0.065 moles) propionyl L-carnitine chloride dissolved in 16 mL water were added.

To the resulting solution 26 g (0.13 moles) dicyclohexylcarbodiimide in 35 mL tetrahydrofuran were slowly added at 0° C. and the mixture was left to react for 48 hours at room temperature.

The mixture was filtered to remove dicyclohexylurea, the filtrate was concentrated to dryness and the oily residue thus obtained was washed with tetrahydrofuran for 18 hours. The solvent was removed by decantation and the oily residue was treated with Et₂O till solidification, then filtered off.

The product thus obtained was dissolved in 100 mL H₂O, and to the resulting solution 5.5 mL concentrated hydrochloric acid solution and 2.5 g 10% Pd/C were added.

The solution was hydrogenated at 3 atmospheres for 18 hours, then filtered and the filtrate lyophilized. The white solid thus obtained was washed with isopropanol for 2 hours.

The resulting mixture was filtered and the solid washed again with $Et_2O$. Following filtration, 1 g of the title compound were obtained.

HPLC: Column Micro-Bondapack $NH_2$
Eluant: $H_2O$-$KH_2PO_4$ 0.05 mM/$CH_3CN$ (35/65)
Flow rate: 1 mL/min
$R_t$: 13.77 min.
$[\alpha]_D^{25} = -17.26$ (c=1.1 $H_2O$)
TLC:
Eluant: ($CHCl_3$ 42.8% isopropanol 28.6%, MeOH 10.7%, $H_2O$ 10.7%, $CH_3COOH$ 7.1%)
$R_F$: 0.54
$H^1NMR(D_2O)$:δ5.75

4.33(1H,m,CHNH)3.68-3.96   (2H,m,$\underline{CH_2}N^+$);
3.22(2H,t,$\underline{CH_2}NH$);   3.2(9H,s,$N^+(\underline{CH_3})_3$);
2.60(2H,d,$\underline{CH_2}CON$); 2.45

$$2H.q. - \overset{O}{\overset{\|}{C}}\underline{CH_2} - CH_3);$$

1.64-1.94(4H,m,—$CH_2$—$CH_2$—); 1.08(3H,t,$\underline{CH_3}$)
$C^{13}NMR(D_2O)$: δ167.688; 167.013; 162.640; 148.680; 59.822; 57.478; 56.238; 45.921; 44.539; 32.481; 30.525; 19.435; 16.444; 15.757.

EXAMPLE 3

Preparation of acetyl L-carnitinamide of L-ornithine chloride (ST 1019).

(M.W. 390.31)
$$(CH_3)_3\overset{+}{N}-CH_2\underset{\underset{OCOCH_3}{|}}{CH}CH_2-CON H\underset{\underset{COOH}{|}}{CH}CH_2CH_2CH_2-NH_3^+ \quad Cl^-$$
$$Cl^-$$

To a suspension of 9.8 g (0.04 moles) acetyl L-carnitine chloride (M.W. 239.70) in 400 mL anhydrous acetonitrile with 16.4 g (0.046 moles) $N^\omega$-benzyloxycarbonyl L-ornithine benzyl ester (M.W. 356.42) [Ann. Chem. 676, 232-37, (1964)]. 12.9 g (0.052 moles) EEDQ (2-ethoxy-1-ethoxycarbonyl-1,2-dihydroquinoline) (M.W. 247.29) were added under stirring at room temperature.

The resulting mixture was kept under stirring at room temperature for 40 hours, the precipitate that formed was filtered off and the filtrate concentrated under reduced pressure at room temperature.

The concentrated solution was added dropwide to 1 L-ethylether under vigorous stirring.

The liquid phase was decanted and the treatment with ethyl ether was repeated on the solid residue dissolved in a small amount of acetonitrile (70 mL).

By decanting the liquid phase a pitchy solid was obtained that was ovendried at 30° C. under a vacuum of 1 mmHg.

20 g acetyl L-carnitinamide of $N^\omega$-benzyloxycarbonyl L-ornithine benzyl ester chloride (M,W, 578.11) were obtained. Yield 86%.

18 g (0.031 moles) acetyl L-carnitinamide of $N^\omega$-benzyloxycarbonyl L-ornithine benzyl ester chloride were dissolved in 100 mL water.

To the solution 2.5 mL conc. HCl and 2 g 10% Pd/C were added and the resulting mixture was hydrogenated under vigorous stirring under 15 atmospheres, at 20° C.

When the theoretically calculated amount of hydrogen had been used up, the suspension was filtered on celite and the filtrate washed with ethyl acetate/ethyl ether. The solvent was then removed under reduced pressure at room temperature.

Following lyophilization, 11 g of the title compound were obtained (Yield 90.5%) as a highly hygroscopic, vitreous white solid.

TLC: single spot.
Eluant: $CHCl_3$:MeOH:$H_2O$:ISOPROH:AcOH 60:40:15:10:15.
Silica gel plates 0.25 mm=60 $F_{254}$ (E. Merck)
Detectors UV: 254 nm and iodine vapours.
Elementary analysis: ($C_{14}H_{29}Cl_2N_3O_5$): Calc %: C 43.08; H 7.49; Cl 18.17; N 10.76; Found %: C 43.24; H 7.23; Cl 17.97; N 10.64.
HPLC: Waters 510 column μBondapack-$NH_2$(10μ), inner diameter=3.9 mm length 300 mm.
Mobile phase: $CH_3CN$/$KH_2PO_4$ 0.05M in $H_2O$ 65:35
Flow rate: 1 ml/min
Detector UV: HP 1040A λ=205 nm
Capacity factor (K')=8.04.
$^1$H-NMR Varian 300 MHz($D_2O$) δ:
1.70-2.01(4H,m,$CH_2CH_2$);   2.14(3H,s,$CH_3CO$);
2.75(2H,d,$CH_2\overline{CONH}$);   3.03(2H,t,$\overline{CH_2}NH_3^+$;
3.20(9H,s,$\overline{N^+(CH_3)_3}$);   3.66(1H,dd,$CH_2\overline{N^+(CH_3)_3}$);
3.90(1H,dd$\overline{CH_2N^+(CH_3)_3}$;   4.33(1H,dd,$\overline{CHNH}$);
5.72(1H,m,$\overline{CHOCOCH_3}$).
$^{13}$C-NMR: Varian 300MHz($D_2O$) (p.p.m): 178.05; 175.43; 173.58; 70.68; 68.57; 56.86; 55.55; 41.78; 41.39; 30.42; 26.16; 23.43.
$[\alpha]_D = -28.7°$ (c=1 in $H_2O$)

EXAMPLE 4

Preparation of acetyl L-carnitinamide of L-citrulline inner salt (ST 1025).

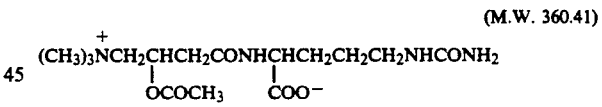

(a) Preparation of $N^\alpha$-benzyloxycarbonyl L-citrulline p-nitrobenzyl ester.

To a solution of 20.5 g (0.066 moles) $N^\alpha$-benzyloxycarbonyl L-citrulline (M.W. 309.32) [J. Am. Chem. Soc. 84, 4943-48(1962)] in 100 mL anhydrous N,N-dimethylformamide, 81.8 mL of a 25% (by weight) methanol solution of tetrabutylammonium hydroxide (M.W. 259.48) were added dropwise under stirring at 0° C.-5° C.

Methanol was then removed by concentrating the solution at room temperature under reduced pressure, then 14.3 g (0.066 moles) 4-nitrobenzylbromide (M.W. 216.04) were added dropwise under stirring while keeping the temperature at 0° C.-5° C.

The mixture was kept under stirring at room temperature for 4 hours, then taken up with 1 L ethyl acetate and the solution thus obtained was washed with water, $NaHCO_3$ saturated solution, water, 0.1N HCl and water again.

The organic solution was dehydrated over anhydrous sodium sulphate and the solvent was removed under vacuum giving a precipitate which was crystallized from an acetone/ethyl acetate mixture and oven-dried under vacuum at 40° C.

25 g N$^\alpha$-benzyloxycarbonyl L-citrulline p-nitrobenzyl ester (M.W. 445.45) were obtained.

M.P. = 144°-146° C.;

Yield: 85%.

(b) Preparation of L-citrulline p-nitrobenzyl ester.

18 g (0.04 moles) N$^\alpha$-benzyloxycarbonyl L-citrulline p-nitrobenzyl ester (M.W. 444.45) were dissolved in 40 mL glacial acetic acid. To the resulting solution 40 mL 30% (by weight) HBr solution (0.2 moles) in acetic acid were added dropwise at 0° C.–5° C.

The mixture was kept at room temperature for 30 minutes, then added to 1.5 L ethyl ether dropwise under stirring.

The oil which formed was separated from the supernatant liquid phase and kept 1 hour under stirring in petroleum ether. After the solvent was decanted, the oil solidified following oven-drying under reduced pressure at 40° C.

14 g (0.036 moles) L-citrulline p-nitrobenzyl ester bromohydrate (M.W. 391.23) were obtained which were suspended in 150 mL anhydrous $CH_2Cl_2$, 10 mL (0.072 moles) triethylamine were added thereto and the resulting mixture kept under vigorous stirring for 30 minutes.

The precipitate was then filtered, washed with $CH_2Cl_2$ and $Et_2O$ and oven-dried under vacuum at 40° C.

8.7 g L-citrulline p-nitrobenzyl ester (M.W. 310.31) were obtained (yield 70%).

(c) Preparation of acetyl-carnitinamide of L-citrulline p-nitrobenzyl ester chloride To a suspension of 5.3 g (0.022 moles) acetyl L-carnitine chloride (M.W. 239.70) and 7.1 g (0.023 moles) citrulline p-nitrobenzyl ester (M.W. 310.31) in 350 mL anhydrous acetonitrile, 7 g (0.028 moles) EEDQ (2-ethoxy-1-ethoxycarbonyl-1,2-dihydroquinoline, M.W. 247.29) were added under stirring at room temperature.

The mixture was kept under stirring at room temperature for 40 hours, the precipitate that formed filtered off and the filtrate concentrated under pressure at room temperature.

The concentrated solution was added to 1.5 mL ethyl acetate dropwise under vigorous stirring.

The liquid phase was decanted and on the solid residue the treatment with ethyl acetate was repeated by dissolving the solid in a small amount of anhydrous dimethylformamide.

Following decantation of the liquid phase, a pitchy solid was obtained that was oven-dried at 30° C. under 1 mm 11 g vacuum.

11 g acetyl L-carnitinamide of L-citrulline p-nitrobenzyl ester chloride (M.W. 532.00) were obtained. Yield 93.5%.

(d) Conversion of acetyl L-carnitinamide of L-citrulline p-nitrobenzyl chloride to ST 1025.

5 g (0.0094 moles) acetyl L-carnitinamide of L-citrulline p-nitrobenzyl ester chloride were dissolved in 50 mL water, to the solution 1 g 10% Pd/C was added and the resulting suspension was hydrogenated at 1.5 atmospheres under vigorous stirring, at 20° C.

When the theoretically calculated amount of hydrogen was used up, the suspension was filtered on celite and the filtrate was treated with 30 mL IRA 402 resin activated as bicarbonate under vigorous stirring for 10 minutes and then eluted through a column.

The resulting turbid solution was washed with ethyl acetate and ethyl ether, and the solvent was removed under reduced pressure at room temperature.

Following lyophilization, 3 g acetyl L-carnitinamide L-citrulline inner salt were obtained as a very hygroscopic, vitreous white solid. Yield 88.5%.

TLC: single spot

Eluant: $CHCl_3$:MeOH:$H_2O$:isoprOH:AcOH 60:40:15:10:15

Silica gel plates: 0.25 mm = 60 $F_{254}$ (E. MERCK)

Detector UV: 254 nm and iodine vapours

Elementary analysis: ($C_{15}H_{28}N_4O_6$): Calc %: C 49.99; H 7.83; N 15.55; Found %; C 49.76; H 7.99; N 15.32.

HPLC Waters 510 Column µBondapack —$NH_2$ (10µ).

Inner diameter: 3,9 mm

Length: 300 mm

Mobile phase: $CH_3CN$/$KH_2PO_4$ 0.05M in $H_2O$ 65:35

Flow rate: 1 ml/min

Detector UV: HP 1040 A λ = 205 nm

Capacity factor (K') = 5.39

$^1$H-NMR Varian 300 MHz($D_2O$)δ = 1.-47–1.88(4H,m,$\underline{CH_2CH_2}$); 2.16(3H,s,$\underline{CH_3}CO$); 2.76(2H,ABX,$\underline{CH_2}CONH$); 3.12(2H,t,$\underline{CH_2}NH$); 3.20(9H,s,N$^+$($CH_3$)$_3$); 3.68(1H,dd,$\underline{CH_2}N^+(CH_3)_3$); 3.93(1H,dd,$\underline{CH_2}N^+(CH_3)_3$); 4.14(1H,dd,$\underline{CH}NH$); 5.71(1H,ABX,$\underline{CH}OCOCH_3$)

$^{13}$C-NMR: Varian 300 MHz($D_2O$)(p.p.m.) = 181.41; 175.30; 172.75; 164.33; 70.59; 68.64; 57.97; 56.70; 42.30; 41.29; 31.69; 28.66; 23;31.

[α]$_D^{25}$ = −22.9 (c−1 in $H_2O$)

EXAMPLE 5

Preparation of acetyl L-carnitinamide of glutamine chloride (ST 1026)

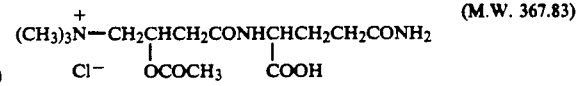

(M.W. 367.83)

To a suspension of 9.8 g (0.4 moles) acetyl L-carnitine chloride in 400 mL acetonitrile containing 5% of water, and 16.1 g (0.046 moles) glutamine benzylester salified with trifluoroacetic acid [Shimamura S. et al., Chem. Pharm. Bull. 30(7), 2433(1982)] and 4.7 g (0.046 moles) triethylamine, 12.9 g (0.052) EEDQ were added under stirring at room temperature.

The resulting mixture was kept under stirring at room temperature for 40 hours. As the reaction proceeded, the mixture dissolved completely. When the reaction ended, the solution was concentrated under reduced pressure at room temperature and then the concentrated solution was added to 1 L ethyl ether dropwise under vigorous stirring. A pitchy solid precipitated which was subjected to treatment with ethyl ether by dissolving it in 70 mL acetonitrile.

The pitchy solid thus obtained was oven-dried at 30° C. under 1 mmHg vacuum.

16.3 acetyl L-carnitinamide of glutamine benzyl ester (M.W. 457.96) were obtained. Yield 89%.

13.7 g (0.03 moles) acetyl L-carnitinamide of glutamine benzyl ester chloride were dissolved in 100 mL $H_2O$.

2 g 10% Pd/C were added to the solution and the resulting mixture was hydrogenated at 1.5 atmospheres under vigorous stirring at 20° C. When the theoretically calculated hydrogen amount was used up, the suspension was filtered on celite and the filtrate was washed with ethyl acetate and ethyl ether. The solvent was then removed under reduced pressure at room temperature. The remaining aqueous solution was lyophilized.

9.9 g acetyl L-carnitinamide of L-glutamine chloride were obtained, as a highly hygroscopic white solid. Yield 90%.

TLC: single spot

Eluant: CHCl₃: MeOH: H₂O: isoprOH: AcOH
         60     40    15    10       15

Silica gel plates: 0.25 mm=60F$_{254}$ (E. Merck)
Detector UV: 254 nm and iodine vapours
Elementary analysis: ($C_{14}H_{26}ClN_3O_6$): Calc %: C 45.71; H 7.13; Cl 9.64; N 11.42; Found %: C 45.62; H 7.34; Cl 9.70; N 11.24.
HPLC
Column Nucleosil 5-SA:
Inner diameter 4 mm;
Length 200 mm;
Mobile phase $CH_3CN/KH_2PO_4$ 0.05M in $H_2O$ (65/35)
pH=4.0
Flow rate 0.75 mL/min
Detector UV: 205 nm
Capacity factor (K'): 9.88
$^1$H-NMR: Varian 300 MHz($D_2O$)δ=1.90–2.22(2H,m,CHC$\underline{H_2}$C$\underline{H_2}$; 2.16(3H,s,C$\underline{H_3}$CO); 2.36(2H,t,C$\underline{H_2}$CON$\overline{H_2}$); 2.73–2.78(2H,m,C$\underline{H_2}$CONH); 3.20(9H,s$\overline{N^+}$(CH₃)₃); 3.63–3.95(2H,m,C$\underline{H_2}$N$^+$(CH₃)₃); 4.23–4.29(1H,m,C$\underline{H}$NH); 5.64–5.75(1H,m,CHOCOCH₃)
$^{13}$C-NMR Varian 300 MHz($D_2O$)(p.p.m.): 181.01; 179.80; 175.31; 173.52; 70.71; 68.60; 56.94; 55.58; 41.42; 34.53; 29.45; 23.48.

EXAMPLE 6

Preparation of isovaleryl L-carnitinamide of L-arginine chloride (ST 1027).

Isovaleryl L-carnitine chloride (4.2 g; 0.015 moles) was dissolved in 100 mL of a 1:1 tetrahydrofuran-methanol mixture.

N$^\omega$-nitro-L-arginine benzyl ester (5.5 g; 0.018 moles) EEDQ (6 g; 0.022 moles) were added to the solution.

The resulting reaction mixture was kept under stirring at room temperature overnight and then concentrated under vacuum. The oily residue thus obtained was dissolved in water and the resulting solution extracted with AcOEt and Et₂O.

The aqueous solution (about 200 mL) containing isovaleryl L-carnitinamide of N$^\omega$-nitro-L-arginine benzyl ester chloride was hydrogenated at 3 atmospheres with 2 g palladium black for 2 hours, then following addition of 1 g palladium black further hydrogenated for 1 hour.

The mixture was filtered and the filtrate lyophilized. 5 g of the title compound as hygroscopic white solid were obtained. Yield 84%.

TLC: Silica gel, detector iodine vapours
Eluant: CHCl₃-isoprOH-MeOH-H₂O-CH₃COOH, 43:29:11:11:7
Rf=0.15
HPLC:
Column μBondapack-NH₂
Eluant: $CH_3CN-KH_2PO_4$ 50 mM (65:35)
R$_t$=8.9 min $[\alpha]_D^{25}$= −10.4 (c=1% H₂O)
NMR$^1$H D₂O δ5.75

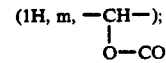

(1H, m, −CH−);

4.25 (1H,m,CH−NH); 3.7–4.0(2H,mnCH₂N+); 3.2–3.0(11H,m+O,C$\underline{H_2}$NH(CH₃)₃);
2.8(2H,m,C$\underline{H_2}$CON$\overline{H}$); 2.4(2H,dd,COCH₂);
2.0(1H,m,C$\underline{H}$(CH₃)₂); 1.6–1.9(4H,m,CH₂CH₂);
0.9(6H,d,CH−(CH₃)₂).

Based on the procedures described in the foregoing examples, further compounds encompassed by the present invention can be easily prepared by performing substitutions on the reactants which will be apparent to the average skilled expert in organic synthesis.

Also changes to the operating conditions with respect to those described in the foregoing examples will be within the reach of the average expert. Thus, for instance in the condensation step, condensing agents such as EEDQ (N-ethoxy-carbonyl-2-ethoxy-1,2-dihydroquinoline) and CDI (carbonyl-diimidazole) can be used; solvents such as acetone, methylene chloride, chloroform, ethylacetate, acetonitrile, dimethylformamide; the reaction temperature can vary between −10° C. and +30° C.; (the dropwise addition of DDC solution is preferable conducted at 0° C./+5° C. and the reaction temperature is comprised between 0° C. and +20° C. The reaction time can vary between 24 and 72 hours and preferably is 48 hours.

In the hydrogenation step further solvents or mixtures of solvents can be used comprising water and lower C₁-C₄ alkanols. The reaction temperature can vary between +15° C. and +30° C. and preferably is +20° C.

PHARMACOLOGICAL STUDIES

Several pharmacological studies were conducted on the compounds of the present invention. The results of some studies relating to the inherent tropic activity of acetyl L-carnitinamide of L-arginine chloride hydrochloride (ST 857) and the enhancement of the action of nerve growth factor (NGF) on PC 12 cells are hereinbelow described.

One event that is common to the physiology and pathophysiology of the aging process in the central nervous system (CNS), is the reduction of the nerve growth factor (NGF) receptors. NGF is a polypeptide that is essential for the development and maintenance of some classes of neurons.

In the CNS, NGF has trophic effects on the magnocellular cholinergic neurons of the basal forebrain and septum. NGF is released by target tissues of cholinergic innervation, such as hippocampus and front cortex, where it binds to the nerve growth factor receptors (NGFR) on cholinergic terminals and is retrogradely transported to the cell soma in the basal forebrain and septum.

The continuous NGF supply warrants neuron survival.

The finding that NGF exerts neurotrophic activity in CNS has led to the hypothesis that the reported loss of NGFR in senescence with the resulting reduction of NGF activity is responsible for neuronal cell death and atrophy. Consequently, the therapeutic use of NGF for the treatment of neurological diseases associated with aging has been proposed. However, since the problems associated with NGF absorbance, transport and stability have not been solved, NGF actual therapeutical utilization meets with serious difficulties.

It is known that the treatment of rats with acetyl L-carnitine ALCAR ® a naturally occurring substance involved in mitochondrial metabolism of fatty acids prevents certain CNS impairments in the aged. ALCAR ® treatment of senescent rats prevents the loss of glucocorticoid receptors in the hippocampus and improves the behavioural performances that are related to the limbic system.

ALCAR ® partially prevents the loss of NGFR that occurs in the hippocampus and the basal forebrain of aged rodents.

ALCAR ® has been shown to stimulate NGFR synthesis and enhance the action of NGF on PC 12 cells.

The rat pheochromocytoma (PC 12) cell line was chosen as an in vitro model system for NGF-responsive neurons. PC 12 cells are a cell line derived from a tumor of rat adrenal medulla that display NGFR similar to those described for sympathetic and sensory neurons, PC 12 typically respond to NGF by elongating neurites and developing into electrically excitable cells featuring some characteristics of the post-mitotic cholinergic neuronal phenotype.

The study reported hereinbelow shows that the action of NGF on PC 12 cells is enhanced by ST 857 treatment more potently than by ALCAR ® treatment. Thus, ST 857 is shown to prevent some degenerative processes in the aged brain by lowering the response threshold of susceptible neurons to neurotrophic factors.

Even more importantly, this study shows that ST 857 possesses inherent tropic activity and is per se effective in stimulating neurite outgrowth, even in the absence of NGF.

Rat pheochromocytoma ((PC 12) cells were grown in RPMI 1640, supplemented with 5% heat inactivated horse serum +5% heat inactivated fetal calf serum at 37° C. in humidified incubator with 5% $CO_2$ atmosphere and fed on alternate days. At subconfluency, cells were dislodged by vigorous shaking and reseeded at 1:1 ratio. Acetyl L-carnitine ALCAR ® and ST 857 were dissolved in RPMI and added to cells at the final concentrations indicated in the various experiments.

NEURITE OUTGROWTH EXPERIMENT

PC 12 cells were plated out into 35 mm Petri dishes at a density $2 \times 10^5$ cells/ml. On the sixth day of either ALCAR ® or ST 857 treatment (1 mM), the cells were added with NGF dissolved in RPMI 1640 at a suboptimal concentration (i.e. ineffective to stimulate neurite outgrowth) of 1 ng/mL (0.037 nM). On day 5 after addition, 100-120 cells from 5-12 randomly chosen microscope fields were counted and assayed for presence of neurites. All the counts were done independently by two investigators on coded samples. After all counts were carried out, codes were broken and the average of the two counts taken as final value estimation. The results are shown in table 1.

TABLE 1

| NEURITIC OUTGROWTH | | |
|---|---|---|
| Control | − | no neurites present |
| control + NGF | −/+ | occasional neuritic outgrowth |
| ST 857 | ++ | neurites present |
| ST 857 + NGF | +++ | abundant neuritic outgrowth |
| ACETYL L-CARNITINE | − | no neurites present |
| ACETYL L-CARNITINE + NGF | ++ | neurites present |

EFFECT OF ST 857 (1mM) ON THE NEURITE OUTGROWTH OF CELLS IN THE PRESENCE OR ABSENCE OR A SUBOPTIMAL NGF DOSE (1ng/mL).
EFFECTS OF ALCAR ® and ST 857 ON CHOLINE ACETYLTRANSFERASE (ChAT).

The method described by Fonnum, F. in "A rapid radiochemical method for the determination of choline acetyltransferase". J. of Neurochem. (1975) vol. 24, 407:409 was used. Briefly, the compounds were added to the culture medium at final concentration of 1 mM.

The cells were grown for 6 days in the presence of ST 857. The medium was changed every other day. On the sixth day the cells were harvested and resuspended directly in a homogenization buffer for ChAT activity assay. Protein content was assayed on an aliquot of the cell suspensions. The results are shown in table 2.

TABLE 2

|  | ChAT nmoli ACh/ mg/hour (in the presence of NGF) | ChAT nmoli ACh/ mg/hour (in the absence of NGF) |
|---|---|---|
| CONTROL | 51.1 ± 6.7 | 16.7 ± 1.7 |
| ST 857 | 140.0 ± 8.9 | 46.6 ± 2.5 |
| ACETYL L-CARNITINE | 133.3 ± 4.4 | 33.3 ± 4.2 |

EFFECT OF ST 857 ON CULTURED HUMAN CORTICAL CELL LINE (HCN-1A).
EFFECT OF ST 857 (1mM) ON THE ACTIVITY OF ENZYME CHOLINEACETYLTRANSFERASE (ChAT) IN PC 12 CELLS IN THE PRESENCE OR ABSENCE OF NGF (10 ng/mL).

The HCN-1A cells are a non-tumoral cell line derived from human cortical neuroblasts which respond to NGF by differentiating into bipolar or multipolar neurite-bearing neurons.

HCN-1A cells show immunoreactivity for different neurotransmitters such as GABA, glutamate, somatostatin, cholecystokinin-8 (CCK-6) and VIP (vasoactive intestinal polypeptide).

Treatment of HCN-1A with ST 857 (1 mM) resulted in neurite outgrowth and cell differentiation toward the neuronal phenotype.

ST 857 induced also GABA immunoreactivity in HCN-1A and formation of functional synapses, both in the presence and in the absence of NGF (10 ng/ml). Furthermore, the NGFR in mRNA was increased in these cells following ST 857 treatment, in a manner similar to that elicited by NGF.

TOLERABILITY

ST 857, administered via the intraperitoneal or oral route, showed to be well tolerated.

In mice, LD50 orally is higher than 2 g/kg; LD50 intraperitoneally is higher than 600 mg/kg.

The compounds of the present invention are orally or parenterally administered, in any of the usual pharmaceutical forms which are prepared via the conventional procedures well-known to those persons skilled in pharmaceutical technology. These forms include solid and liquid oral unit dosage forms such as tablets, capsules, solutions, syrups and the like as well as injectable forms, such as sterile solutions for ampoules and phials.

For these pharmaceutical forms the usual solvents, diluents and excipents are used. Optionally, sweetening, flavouring and preservative agents can also be present. Non limiting examples of susch agents are sodium carboxymethylcellulose, polysorbate, mannitol, sorbitol, starch, avicel, talcum and other agents which will apparent to those skilled in the pharmaceutical technology.

The dose which is administered will be determined by the attending physician having regard to the age, weight and general conditions of the patient, utilizing sound professional judgement. Although effective results can be noticed at doses as low as 5 to 8 mg/kg of body weight daily, a dose of from about 10 to 50 mg/kg of body weight is preferred. Whenever necessary, larger doses can be safely administered in veiw of the low toxicity of the compounds of this invention.

Therefore, pharmaceutical compositions in unit dosage form comprise from about 50 to about 500 mg of a compound of formula (1).

We claim:

1. An amide of alkanoyl L-carnitine of Formula (I):

$$(CH_3)_3{}^+NCH_2CHCH_2COR'$$
$$X^- \quad OR$$
(I)

wherein R is a straight or branched alkanoyl group having from 2 to 8 carbon atoms selected from the group consisting of acetyl, propionyl, butyryl, isobutyryl, valeryl, isovaleryl, hexanoyl, 1-methylbutyryl, t-butylacetyl, 2-ethylbutyryl, 3-methylvaleryl, 4-methylvaleryl, 2-ethylhexanoyl and 2-propylpentanoyl; R' is the monovalent residue of a naturally occurring aminoacid selected from the group consisting of:

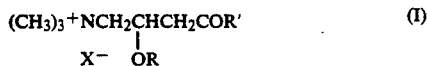
—NHCH(CH$_2$)$_n$NH$_3^+$ X$^-$; wherein n = 3 or 4;
|
COOH

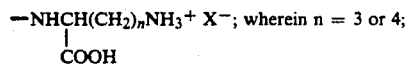
—NHCH(CH$_2$)$_3$NHC(=NH)NH$_3^+$ X$^-$;
|
COOH

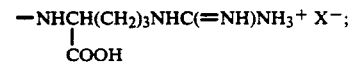
—NHCH(CH$_2$)$_3$NHCONH$_2$;
|
COOH

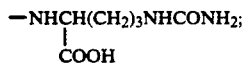
—NHCH(CH$_2$)$_2$CONH$_2$; and
|
COOH and X$^-$ is the anion of a pharmacologically acceptable salt.

2. The amide of claim 1, wherein X$^-$ is selected from chloride, bromide, iodide, orotate, acid aspartate, acid citrate, acid phosphate, acid fumarate, lactate, acid maleate, acid oxalate, acid sulphate and glucosephosphate.

3. The amide of claim 1, wherein R is acetyl and R' is

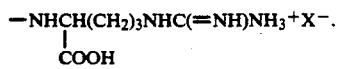
—NHCH(CH$_2$)$_3$NHC(=NH)NH$_3^+$X$^-$.
|
COOH

4. The amide of claim 1, wherein R is propionyl and R' is

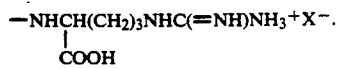
—NHCH(CH$_2$)$_3$NHC(=NH)NH$_3^+$X$^-$.
|
COOH

5. The amide of claim 1, wherein R is isovaleryl and R' is

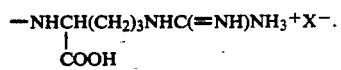
—NHCH(CH$_2$)$_3$NHC(=NH)NH$_3^+$X$^-$.
|
COOH

6. The amide of claim 1, wherein R is acetyl and R' is

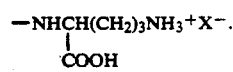
—NHCH(CH$_2$)$_3$NH$_3^+$X$^-$.
|
COOH

7. The amide of claim 1, wherein R is acetyl and R' is

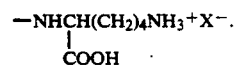
—NHCH(CH$_2$)$_4$NH$_3^+$X$^-$.
|
COOH

8. The amide of claim 1, wherein R is acetyl and R' is

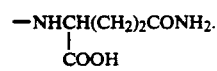
—NHCH(CH$_2$)$_2$CONH$_2$.
|
COOH

9. The amide of claim 1, wherein R is acetyl and R' is

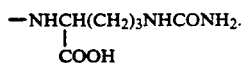
—NHCH(CH$_2$)$_3$NHCONH$_2$.
|
COOH

10. The amide of anyone of claim 3 to 9, wherein X$^-$ is chloride.

11. A amide of claim 9, wherein the amino acid radical is in zwitterionic form.

12. An orally or parenterally administrable pharmaceutical composition comprising an amide of claim 1, as active ingredient and a pharmacologically acceptable excipient.

13. An orally or parenterally administrable pharmaceutical composition for promoting regeneration of the nervous tissue, inhibiting neuronal degeneration, enhancing the processes of learning and memory and for the treatment of coma, comprising an amide of claim 1, as active ingredient and a pharmacologically acceptable excipient.

14. The composition of claim 13 in unit dosage form comprising between about 50 and about 500 mg of an amide of claim 1.

* * * * *